(12) United States Patent
Pollack

(10) Patent No.: US 10,012,661 B2
(45) Date of Patent: Jul. 3, 2018

(54) HIGH DENSITY IN SITU BARCODE READING SYSTEM

(71) Applicant: Siemens Healthcare Diagnostics Inc., Tarrytown, NY (US)

(72) Inventor: Benjamin Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 122 days.

(21) Appl. No.: 15/111,295

(22) PCT Filed: Jan. 23, 2015

(86) PCT No.: PCT/US2015/012581
§ 371 (c)(1),
(2) Date: Jul. 13, 2016

(87) PCT Pub. No.: WO2015/112794
PCT Pub. Date: Jul. 30, 2015

(65) Prior Publication Data
US 2016/0327583 A1    Nov. 10, 2016

Related U.S. Application Data

(60) Provisional application No. 61/931,337, filed on Jan. 24, 2014.

(51) Int. Cl.
*G01N 35/02* (2006.01)
*G01N 35/00* (2006.01)
(Continued)

(52) U.S. Cl.
CPC ...... *G01N 35/00732* (2013.01); *B01L 3/5453* (2013.01); *B01L 9/06* (2013.01);
(Continued)

(58) Field of Classification Search
CPC ....... G01N 35/00732; G01N 35/00722; G01N 35/00584; G01N 35/026; G01N 35/02;
(Continued)

(56) References Cited

U.S. PATENT DOCUMENTS 5,700,429 A   12/1997   Buhler et al.
7,807,448 B2  10/2010   Glezer et al.
(Continued)

FOREIGN PATENT DOCUMENTS

CN    101031934 A    9/2007
CN    101529448 A    9/2009
(Continued)

OTHER PUBLICATIONS

Extended EP Search Report dated Apr. 7, 2017 of corresponding European Application No. 15740331.2, 6 Pages.
(Continued)

*Primary Examiner* — Christine T Mui

(57) ABSTRACT

Methods and systems are provided that allow scanning of barcode information on sample vessels in situ in a tray. A laboratory instrument includes one or more trays, each having a plurality of recesses, which are configured to hold a plurality of sample vessels, and a plurality of openings between the recesses. The instrument further includes one or more rods that are separate from the trays, each having optical elements configured to read barcode information on the sample vessels. The rods are configured to move through the plurality of openings.

23 Claims, 9 Drawing Sheets

(51) Int. Cl.
*G06K 7/14* (2006.01)
*B01L 9/06* (2006.01)
*B01L 3/00* (2006.01)
*G06K 7/10* (2006.01)
*G06K 19/06* (2006.01)
*G06K 17/00* (2006.01)
*G01N 35/04* (2006.01)

(52) U.S. Cl.
CPC ....... *G01N 35/026* (2013.01); *G06K 7/10861* (2013.01); *G06K 7/1413* (2013.01); *G06K 19/06028* (2013.01); *B01L 2300/021* (2013.01); *G01N 2035/00752* (2013.01); *G01N 2035/0418* (2013.01); *G06K 7/10693* (2013.01); *G06K 2017/0087* (2013.01)

(58) Field of Classification Search
CPC .... G01N 35/00; G06K 7/1413; G06K 7/1408; G06K 7/1404; G06K 7/14
USPC ................................ 436/47, 43; 422/400, 50
See application file for complete search history.

(56) References Cited

U.S. PATENT DOCUMENTS

| | | | |
|---|---|---|---|
| 7,931,201 | B2 | 4/2011 | Zhang et al. |
| 8,028,843 | B2 | 10/2011 | Guzman et al. |
| 2002/0040934 | A1 | 4/2002 | Itou et al. |
| 2002/0125324 | A1 | 9/2002 | Yavid et al. |
| 2004/0258565 | A1 | 12/2004 | Watari |
| 2005/0247790 | A1 | 11/2005 | Itoh |
| 2006/0000296 | A1* | 1/2006 | Salter ........................ B01L 9/06 73/863.01 |
| 2009/0129990 | A1 | 5/2009 | Kokawa et al. |
| 2010/0025464 | A1 | 2/2010 | Trueeb et al. |
| 2010/0294050 | A1 | 11/2010 | Massaro |
| 2011/0115610 | A1 | 5/2011 | Hughes |
| 2013/0209995 | A1 | 8/2013 | Andrulat et al. |
| 2013/0306729 | A1 | 11/2013 | Dilks et al. |

FOREIGN PATENT DOCUMENTS

| | | |
|---|---|---|
| CN | 102192990 A | 9/2011 |
| CN | 202177910 U | 3/2012 |
| WO | 2012/127869 A1 | 9/2012 |
| WO | 2013/116661 A1 | 8/2013 |
| WO | 2014/145157 A1 | 9/2014 |

OTHER PUBLICATIONS

PCT International Search Report and Written Opinion dated Apr. 15, 2015 (6 Pages).

\* cited by examiner

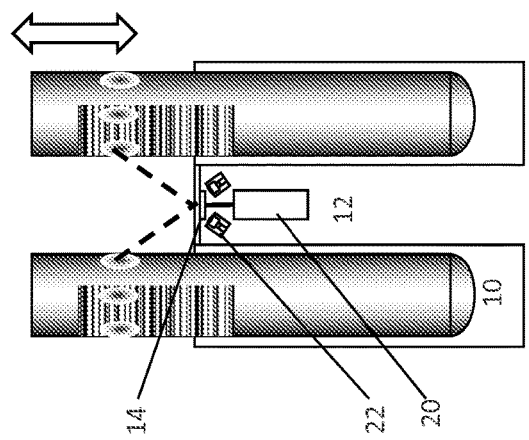
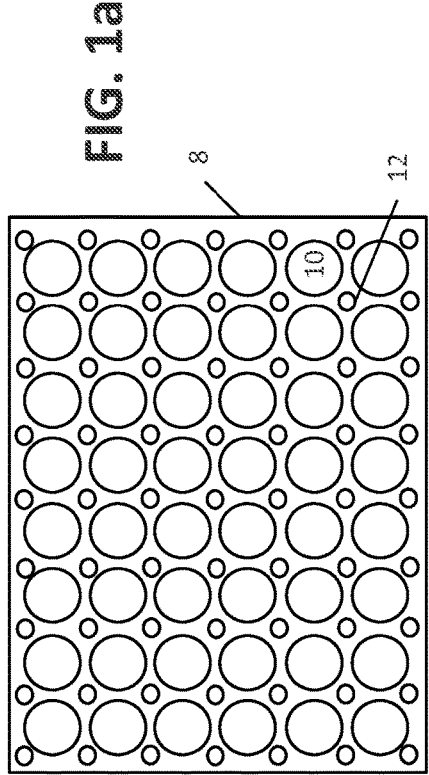
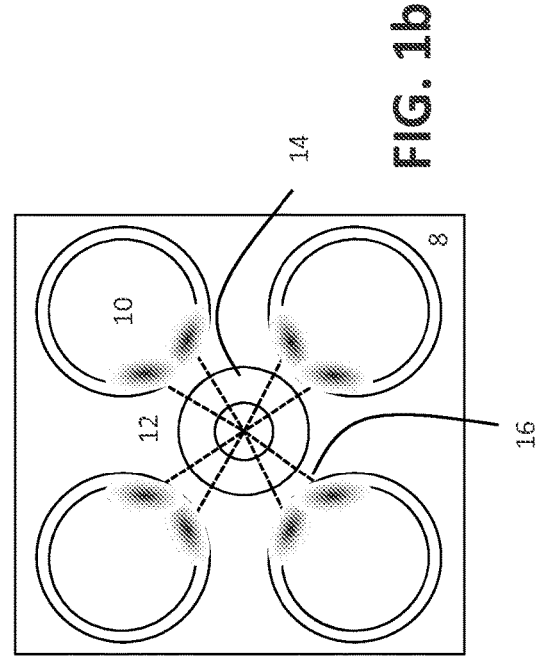

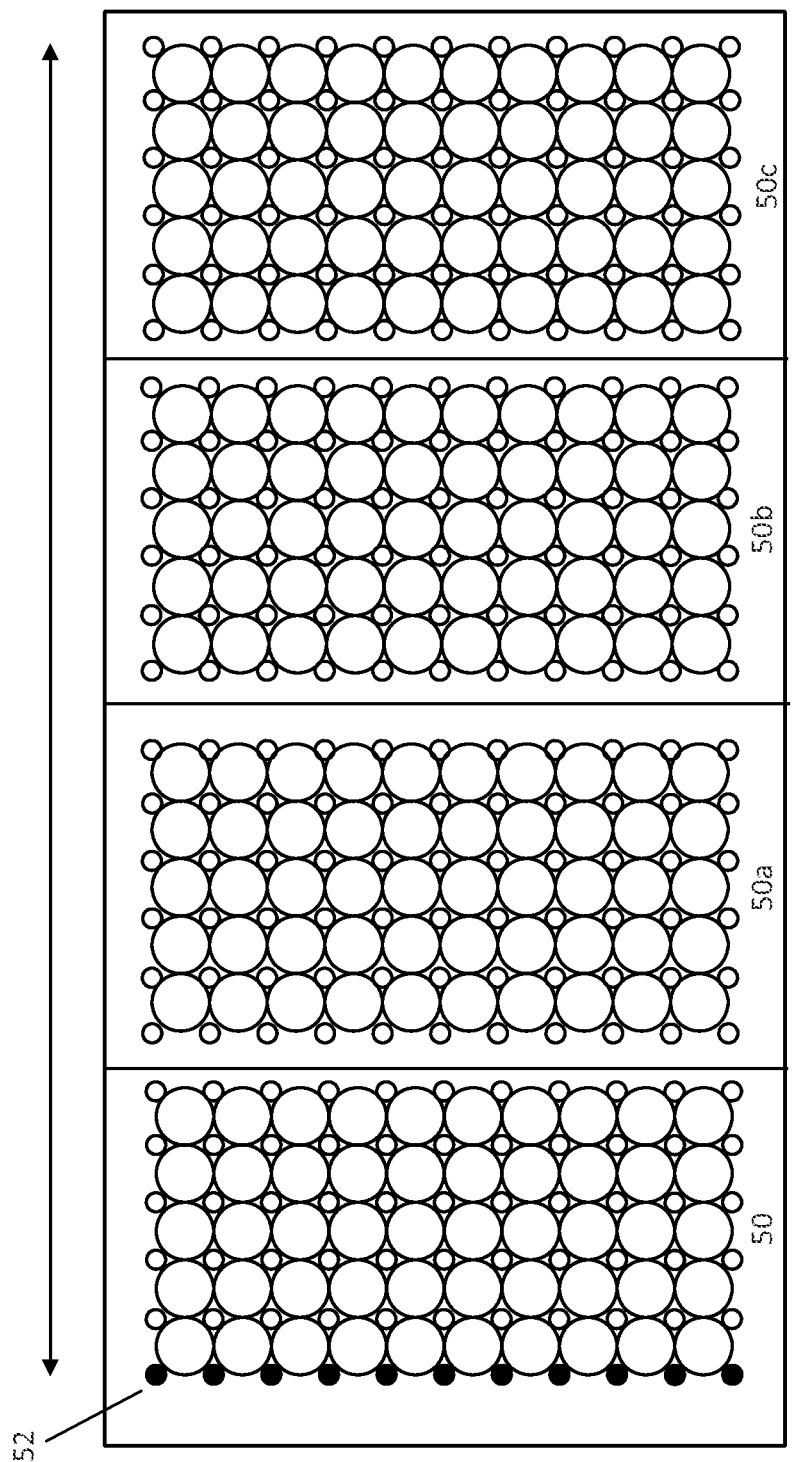

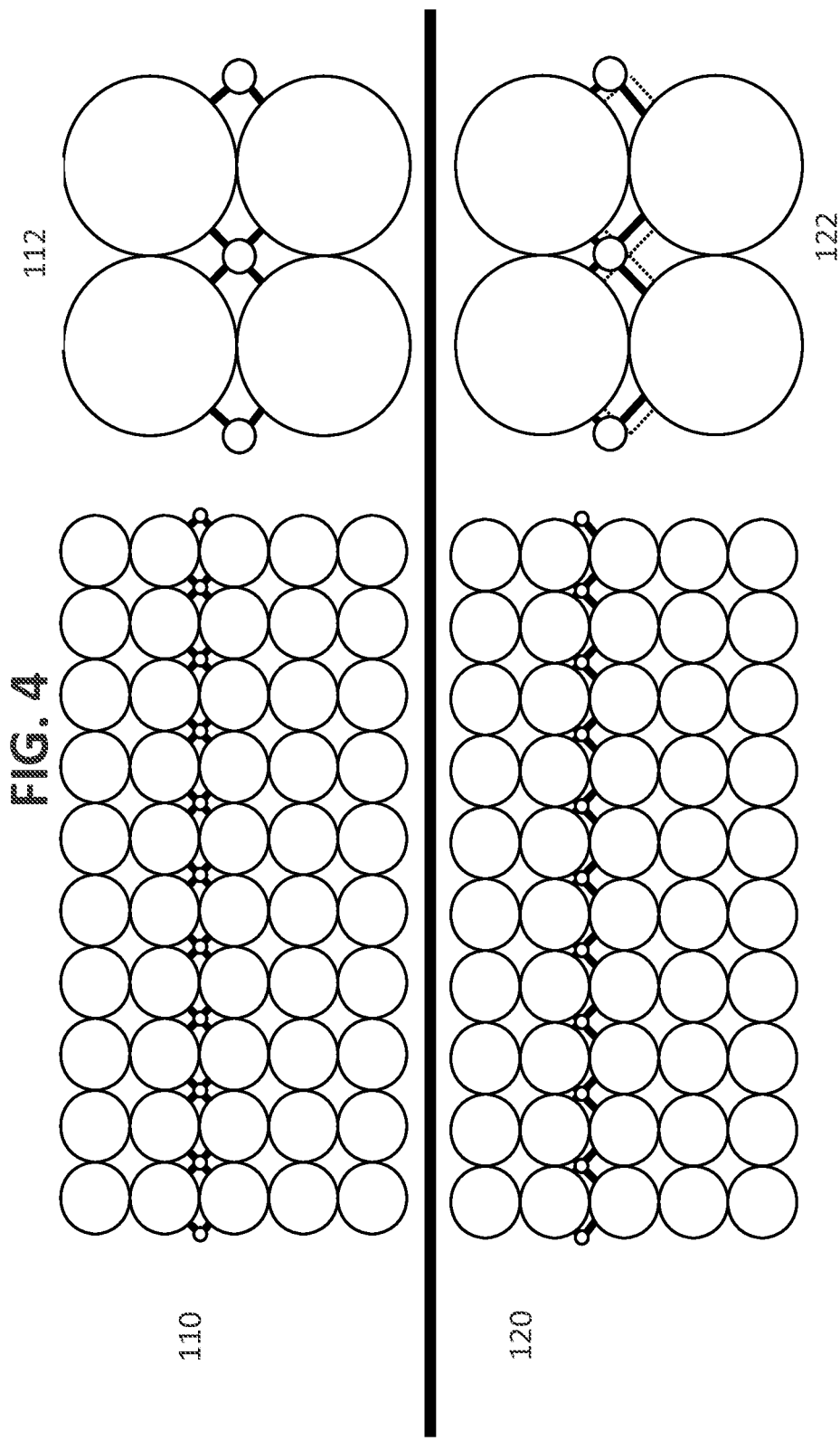

HIGH DENSITY IN SITU BARCODE READING SYSTEM

CROSS REFERENCE TO RELATED APPLICATIONS

This application claims priority to U.S. provisional application Ser. No. 61/931,337 filed Jan. 24, 2014, which is incorporated herein by reference in its entirety.

TECHNOLOGY FIELD

The present disclosure relates to a barcode scanning systems for use with fluid sample vessels.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) into which tubes or vials containing patient samples have been loaded.

IVD systems that process a large number of test tubes (both analyzers and automation equipment) require test tube racks that enable high-density transport and storage. Generally these tubes have barcode identifiers in the form of stickers on the outside of the tube. These barcodes are used to identify samples, allowing humans and automation systems to determine how to process sample tubes. To read these barcodes, typically an optical barcode reader/scanner is used. However, a barcode reader requires line-of-sight access to a large portion of the surface of a tube in order to read it, meaning that typically tubes must be physically removed from racks or storage trays. One alternative may include a rack that allows all of its tubes to be read in situ, via openings in the structure of the tube holders. These racks require that every tube to sit on an exterior edge, limiting the rack to a low-density one or two row design.

If a rack does not support in situ barcode reads, then each tube must be mechanically removed from the rack and transported to a barcode reader at some point in the process. If the tube is immediately processed after the barcode is read, then the cycle time impact is minimized, but a first-in-first-out (FIFO) scheduling algorithm is imposed on the overall system which may negatively impact throughput and resource utilization. If the tube is returned to the rack after its barcode is read, then a non-FIFO scheduling algorithm can be used, but the cycle time impact will be much larger. Therefore, there exist competing requirements for high-density racks, low cycle time impact, and look-ahead scheduling, which are not satisfactorily met in the existing art.

For both analyzers and automation equipment, there is a need to process a large number of test tubes. To save space in the lab, it is typically ideal to have high density tube storage for loading and unloading the tubes. However, once trays grow beyond a simple one-dimensional tube holder, tube tray, or tube rack, the barcodes become blocked within these storage apparatus. There may be no line of sight to tube labels from the outside of the tray because the interior rows of the tray are blocked by the exterior rows of the tray.

If the tray is such that it does not allow an in situ barcode reading, then there are currently a couple different solutions. One is that when an operator or sample handler singulates the tubes (i.e., when tubes are individually removed from the tray), a fixed scanner can read the barcode before the tubes are placed back in the tray. The location of the tube can be associated with the tube. This allows for random access scheduling and random access processing of the tubes, but it adds an extra processing step (e.g., a barcode reading step) to the process, and this reduces throughput and overall efficiency. Another way is that tubes can be singulated directly to the processing station, allowing that station to discover the tube's identity at the processing station. This imposes a first-in, first-out (FIFO) processing order, which prevents various efficient algorithms and other optimizations, but does not require any extra tube transfer cycle time for a dedicated barcode reading step.

Past systems have made different tradeoffs. For example, systems using high-density racks (50 tubes) and look-ahead scheduling may devote more than 20% of its cycle time to barcode reading. Systems using high-density racks that have a low cycle time impact generally process tubes using a FIFO scheduling algorithm. Most of the analyzers have low cycle time impact and look-ahead scheduling, but low-density racks (e.g., a one dimensional rack might hold five tubes).

SUMMARY

Embodiments provide a barcode reader that allows multiple perspectives of tubes in a tray, without requiring tubes to be removed from the tray. In one embodiment, a laboratory instrument includes one or more trays, each having a plurality of recesses, which are configured to hold a plurality of sample vessels, and a plurality of openings between the recesses. The instrument further includes one or more rods that are separate from the trays, each having optical elements configured to read barcode information on the sample vessels. The rods are configured to move through the plurality of openings.

According to one aspect of some embodiments, the rods are part of a station configured to identify the plurality of sample vessels as part of an IVD workflow. The station can be a standalone barcode reading station, or part of an analyzer and is accessible by an automation system that is configured to transport samples within the analyzer. According to another aspect, the optical elements are configured to read the barcode information substantially perpendicularly. According to another aspect, the optical elements are configured to read the barcode information while the rods move relative to the tray. According to another aspect, the optical elements are configured to automatically rise from below the one or more trays after each tray is placed above the rods. According to another aspect, the optical elements are configured to enter the plurality of openings from above the one or more trays.

According to another aspect, the rods are fixed and configured to read barcode information while the one or more trays are lowered onto the rods. According to another aspect, the rods are configured to enter the plurality of openings from above the one or more trays while the trays are raised to the rods. According to another aspect, the rods comprise an array of rods configured to allow all the sample vessels to be scanned substantially simultaneously. According to another aspect, the rods comprise at least one row of rods configured to allow all the rows of sample vessels to be scanned sequentially.

According to another embodiment, a method for scanning optical information on a plurality of sample vessels includes placing a tray of sample vessels for scanning, and moving at least one rod into and out of openings of the tray. The tray includes a plurality of openings, each configured to receive a rod that contains a plurality of optical elements. The method further includes scanning optical information on each sample vessel as the at least one rod moves relative to the tray.

According to one aspect of some embodiments, the method includes moving an array of rods into all of the plurality of openings substantially simultaneously, and scanning optical information of all of the plurality of the sample vessels substantially simultaneously.

According to another aspect, the method includes moving at least one row of rods into at least one row of the plurality of openings substantially simultaneously. According to another aspect, the method includes moving a single rod into at least one row of the plurality of openings sequentially. According to another aspect, the method includes scanning optical information of at least one row of the plurality of the sample vessels substantially simultaneously. According to another aspect, the method includes moving comprises moving the at least one rod from below the tray. According to another aspect, the method includes moving the at least one rod from above the tray. According to another aspect, the method includes lowering the tray onto the rods. According to another aspect, the method includes adjusting the motion of the at least one rod to allow the rod to travel in multiple available scan paths with at least one of the plurality of openings. According to another aspect, the optical information is barcode information.

BRIEF DESCRIPTION OF THE DRAWINGS

FIGS. 1a to 1c are top and cross sectional views of an exemplary section of a tray for use with some embodiments;

FIG. 3 is a top view of an exemplary barcode reading station for use with some embodiments;

FIG. 4 is a diagrammatic top view of various scan paths for use with some embodiments;

DETAILED DESCRIPTION

Figure 2A:
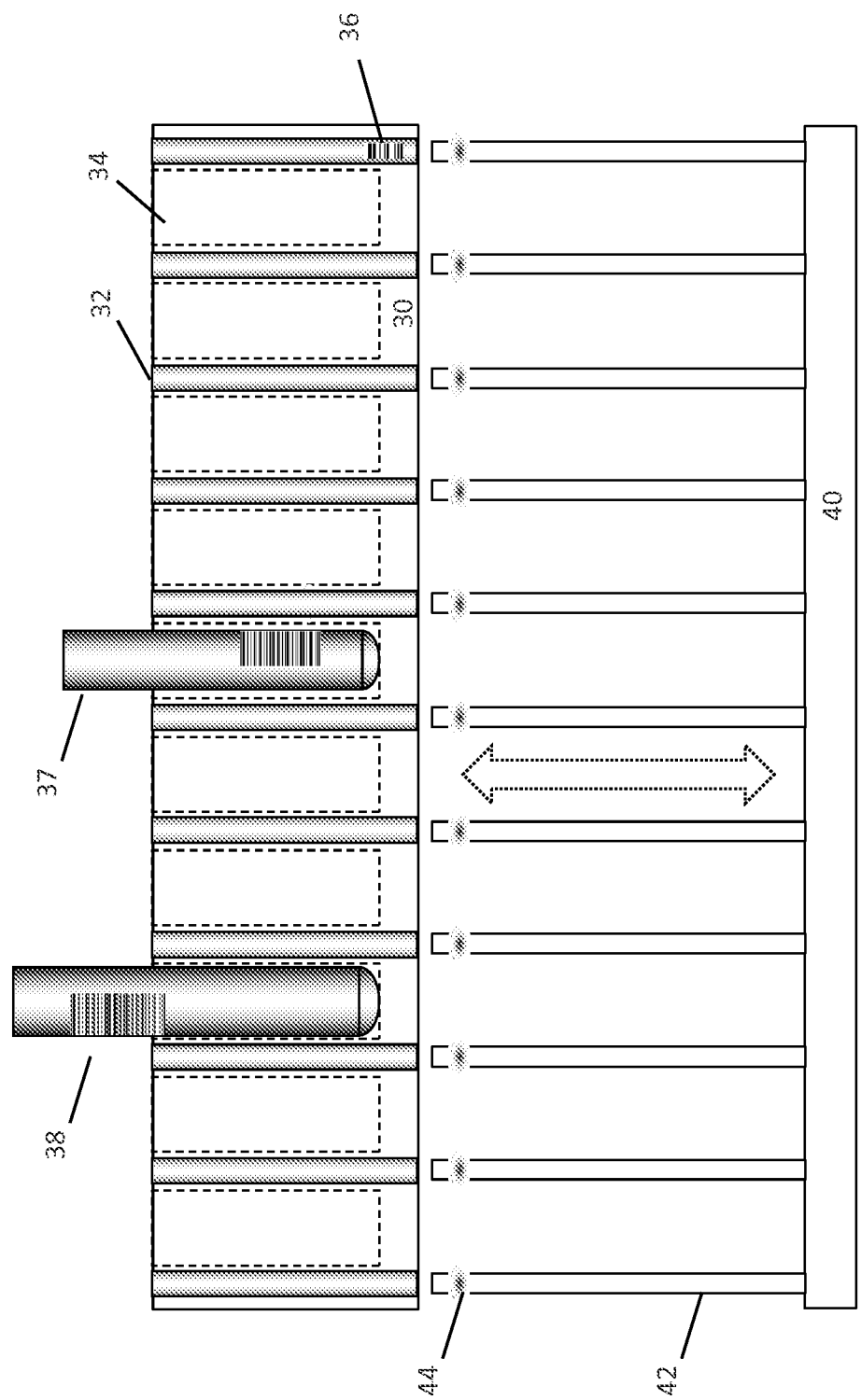
FIGS. 2a to 2c are cross sectional side views of a barcode reading station for use with some embodiments.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Processor: A processor may refer to one or more processors and/or related software and processing circuits. This may include single or multicore processors, single or multiple processors, embedded systems, or distributed processing architectures, as appropriate, for implementing the recited processing function in each embodiment. A processor should be understood as a hardware device.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

An improvement over the described art is a barcode reading test tube holder, described in concurrently owned application PCT/US13/24362, which is incorporated herein by reference. This example includes a barcode reader in a rack that incorporates optics and electronics directly inside the rack itself. This design utilizes miniaturized optics that are installed inside the tray that read the barcodes on the tubes as they are being inserted or removed from the tray.

An exemplary barcode reading test tube holder that can be integrated into a tray or rack is shown in FIGS. 1a-1c. Tray 8 includes a plurality of tube holders 10, which are arranged in a plane, in any reasonable pattern that allows tube holders to be arranged in a spatially dense order adjacent to one another, such as in a rectilinear grid or in a hexagonal pattern. Each tube holder may also be described as a logical slot. Optics 12 are placed between adjacent tube holders, such as at a location adjacent to two to four tube holders. For any reasonably larger tray there will be a similar number of optics 12 as tube holders 10. In some embodiments, where a tray includes a grid of n by m tube holders, there will be (n+1) by (m+1) optics arranged at the edges and amongst adjacent tube holders, allowing the optics to view each tube in the tube holders from four perspectives (for a rectilinear grid). For a hexagonal pattern, where adjacent rows are offset such that each tube holder is a member of three lines of tube holders, separated by sixty degrees, such that tube holders (not at the edge) to have six adjacent tube holders, optics placed between each set of three tube holders can provide six perspectives of each tube. These arrangements ensure at least one unobstructed view via the optics of any label placed on the side of each tube.

Exemplary optics 12 can be understood with respect to FIGS. 1b and 1c. Optics 12 includes a lens structure 14 which allows the distribution of a plurality of beams 16. Beams 16 shine radially, illuminating the tubes in tube holders 10. This allows the optical observation of any labels that is oriented in the illumination plane of beams 16. By arranging a grid of optics 12 interstitially with a grid of tube holders, a plurality of illumination planes from beams multiple sets of beams 16 allow substantially all of the surface of each tube to be scanned, such that a label, such as a barcode label, can be read, regardless of the radial orientation of the label on the tube.

Optics 12 can further include a light source 20, such as a laser source, that shines light onto lens structure 14. Lens structure 14 can include a prism, mirrors, beam splitter, diffraction grating, or other optical structure suitable for radially distributing light from light source 20. Imaging device(s) 22 detect light reflected by the surface of the tubes being scanned. Exemplary imaging devices include photo detectors, cameras, or other suitable imaging devices. Imaging devices 22 can output to a processor to read the barcode information captured. Imaging information from multiple imaging devices from multiple optical devices 12 that are configured to view the same tube can be correlated by a processor to determine the complete barcode information for each tube.

Optics 12 can be embedded in the tube tray itself, such as the optics described in concurrently owned application PCT/US13/24362, which describe exemplary structures for used as optics 12. This allows the tray to read each tube's barcode without the need for external line-of-sight, such as needed by prior art one-dimensional racks. In this manner tubes do not have common drawbacks of prior art, such as needing to be removed from a tube holder slot and/or needing the tube holder slot to have a side-view opening to allow external, in situ scanning (where the label must be properly aligned with the opening.

In some embodiments, the optics 12 are not fixedly embedded into the tray 8. Removable optics can be useful for overcoming certain drawbacks that may occur in certain instances of embedded optics. For example, fixed optics may encounter difficulty reliably reading the low-quality barcodes that are encountered in the field and may be limited in their field of view, preventing optics fixed to the tray from scanning over the entire 75 mm range for barcode labels on a 100 mm tube. For example the optics shown in FIG. 1c utilize a steep angle for viewing the label, which may prevent the beam from scanning the entire height of the tube.

With optics at a fixed position, while inserting the tubes, the optics may need to read the tubes at a very oblique angle, as shown in FIG. 1c. The laser beams may need to scan the label at a very steep angle, which can require high quality lasers with enough coherence to all barcodes to be resolved. Alternatively, the angle may be bounded, requiring an operator to place labels within a certain region on each tube. This may be undesirable.

Fixed optics may also scan the labels when an operator or robot arm inserts the tubes into each slot. This can require that the insertion occurs within defined tolerances. For example, scanning during may require avoiding tilting the tube or changing the speed while inserting, and require that the tube is inserted substantially vertically. These tolerances may be suitable for a robot insertion, but may not be reliable for manual insertion.

If scanning during insertion, the optics only have a single shot at reading each label. The scan path of a laser can be narrow. If there are any kind of imperfections in the barcode on the exact scan path of the optics, there may be no way to generate another scan path short of requiring another insertion. By way of comparison, a traditional laser barcode reading system rotates the tube in front of the laser, while a 2D imager provides a large segment of the barcode to analyze in post processing. Accordingly, in some embodiments 2D imaging optics and sensors may be desirable.

Some embodiments address these limitations of optics fixed in the tray by providing optics that can be inserted into the tray for reading barcode labels, utilizing similar miniaturized optics techniques. By separating the optics from the trays themselves, trays may be constructed more cheaply and a single set of optics can be reused for scanning multiple (or all) trays in a lab. In some embodiments, separating the optics from the tray bifurcates the system of FIGS. 1a-1c into two distinct elements—a fixed barcode reading station and one or more mobile test tube holding devices (e.g. trays or racks). In these embodiments, the test tube holding device, hereafter referred to as a tray, contains no barcode reading electronic components, although it may contain tube presence-sensing components to maintain chain of custody. The barcode reading station comprises of a series of one or more rods embedded with miniaturized barcode reader elements. These rods can be raised and lowered through holes in the tube tray in order to read the barcodes in situ. It will appreciated that raising the rods relative to the tray can be achieved by raising the rods while holding the tray at rest or vice versa.

Figure 2B:
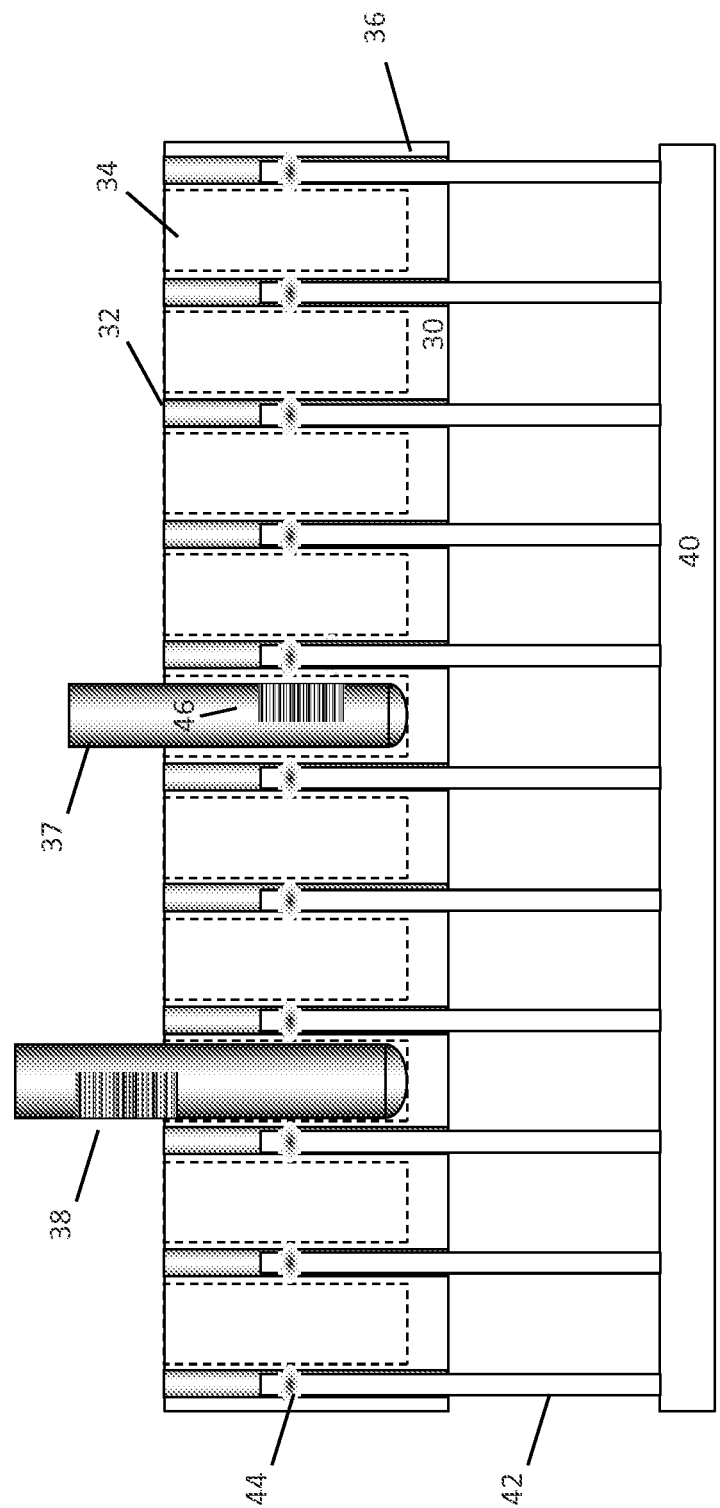
Figure 2C:
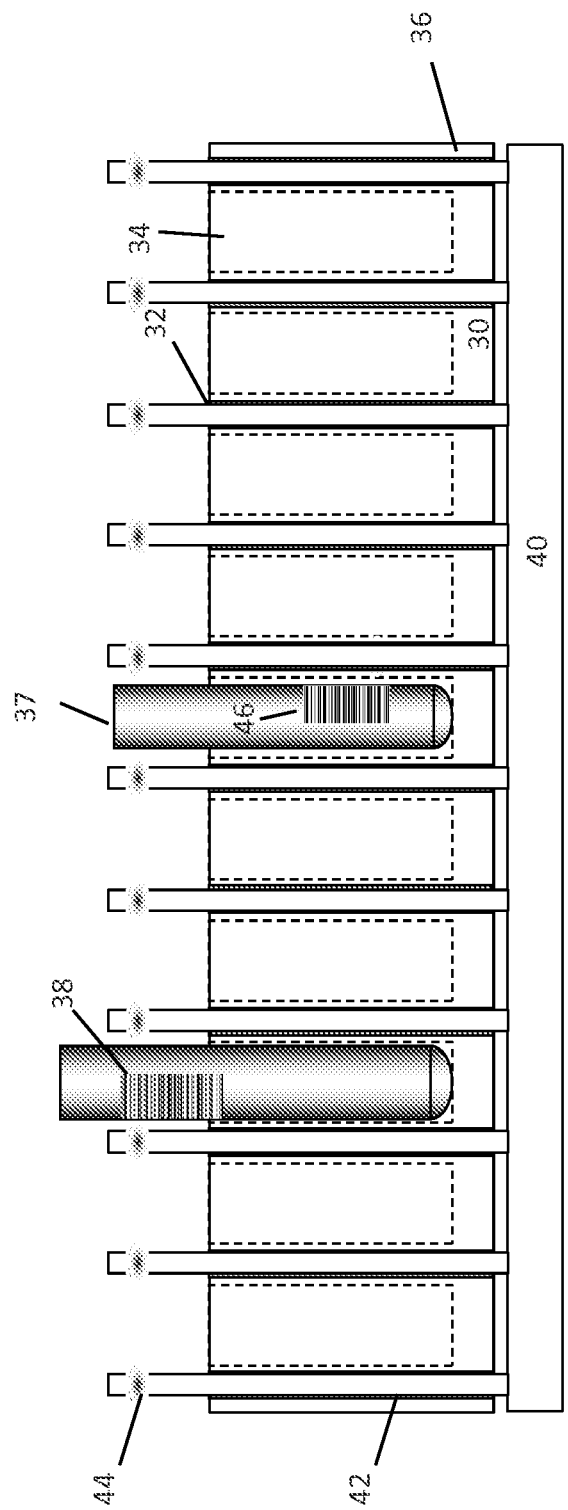

An example of separate optics that can be inserted in to a tray is shown in the side views of FIGS. 2a-2c. FIG. 2a shows the optics and tray before the optics are inserted; FIG. 2b shows the optics partially inserted; and FIG. 3 shows the optics fully inserted into orifices in the tray. Tray 30 includes a main body, which may be made of a plastic or other suitable material, and formed to include openings 32 placed between tube holder slots 34. Openings 32 are configured to receive optics from barcode reading stations. Tube holding slots 34 are configured to receive and hold a plurality of sample tubes 37. Tray 30 may include identifying marks that can be read by the barcode reading station, such as barcode 36, which may be placed in one of the openings 32 or in any other location that allows the optics of the barcode reading station to read the barcode when the optics are inserted into tray 30. Preferably, barcode 36 is placed in a location that allows it to be easily distinguished from barcode labels 38 on sample tubes 37. As shown, barcode labels 38 may be oriented at different positions on tube 37, depending on how a tube is oriented when inserted. By providing a plurality of openings 32 to facilitate the insertion of optics at multiple locations, multiple views of the same tube can be achieved, allowing optics to read barcode labels 38 regardless of orientation. Openings or transparent structures between openings 32 and slots 34 can be used to allow the reading of barcodes that are seated within slots 34. Because the openings are only used to provide line of sight to the optics openings 32, it will be appreciated that slots 34 can have sufficient structure to support sample tubes. In this example, tray 30 is a passive tray and an active station or reader can interact with the tray.

Barcode reading station 40 is an active station used to read barcodes 38 of tubes 37 in slots 34. Station 40 includes a plurality of rods 42, each having optical elements 44, that are configured to be inserted into openings 32. These optical elements can include any of the optical elements discussed throughout, including a combination of lenses/mirrors, light source, and optical sensors. Rods 44 can be inserted into openings 32 by lowering tray 40 or by raising rods 44.

In some embodiments, station 40 includes an aligning surface for placing tray 30. This surface can have openings that align with the openings 32 of tray 30. Once the tray is aligned on the aligning surface of the station, a button or sensor can trigger an automatic motion system, that lifts the rods up through the tray up and back down to perform the scan. This motion system can lower the aligning surface, such that tray 30 descends onto rods 42 or a lift that pushes rods 42 through the aligning surface to raise the rods through openings 32. The motion system can include pneumatic lifts, hydraulic lifts, linear motors, or the like. In some embodiments, the process of scanning up and down can take on the order of three to five seconds. An operator or automation system aligns tray 30 with rods 42; the rods would rise up and come back down. The vertical motion can occur at substantially constant speed during a scan because it is subject to processor and mechanical control. The scan occurs while the tubes are being held in one orientation substantially motionless with respect to the tray, such that the tube angle does not substantially change during a scan. Because the environment of the scan can thus be controlled, a reading station, such as station 40, can improve the reliability without increasing the cost and help reduce cost.

In the configuration of FIG. 2a, tray 30 is aligned with station 40, such that rods 42 align with openings 32. In FIG. 2b, rods 42 rise upward relative to tray 30, preferably at a substantially constant velocity. In this example, the optical elements 44 pass by barcodes that are within the cavities of sample tube holder slots 34. Tube holder slots 34 can include slits that allow adjacent rod openings to have a line of sight into each tube holder slot 34. FIG. 2c shows an arrangement when rods 42 have completed their vertical scan, passing through tray 30, allowing optical elements 44 to read barcodes 38 that are substantially above the surface of the tray. The length of rods 42 can be chosen such that they complete their range of travel at or above the maximum height of barcode information on the tallest sample tube type supported. Upon completing the vertical scan, rods 42 retreat, allowing an optional downward scan.

The motion of rods 42 relative to tray 30 can be driven by automatic motion systems, such as linear motors, hydraulic systems, etc. controlled by a processor to move the tray or rods at a substantially constant speed. In some embodiments, the motion can be controlled by an operator who manually descends the tray onto the rods.

In some embodiments, the tray is substantially passive with no active electronics. In some embodiments the tray includes some active or electronic components to allow tube presence sensing. This can include switches for each tube holder in the tray or an IR sensor inside of each slot that can detect whether a tube has been removed. These sensors or switches can be any reasonable device suitable for sensing the sample. Adding presence sensing allows the tray to detect whether anyone has removed or added a tube since the last reading. Presence sensors allow a tray or laboratory information system to determine that a previously scanned sample tube has been removed and that the identity of any sample in that tray slot is unknown. A processor now knows that at least that one slot needs to be rescanned before proceeding. Accordingly, switches in the tray can be used as chain of custody sensors.

An example of an active system for sensing the presence of a tube is to use a pulsed optical proximity sensor for each tube slot in a tray. A low power near infrared light source pulses on a regular basis and the reflected light is observed with a photo detector. The light source may be pulsed every few seconds for a few milliseconds. This results in a very low duty cycle (e.g., 0.015%, or 13 seconds per day total illumination). This can result in very little power consumption.

By separating the barcode reading from the tray itself, it allows a lab to have many cheaper or simpler trays for holding and transporting sample tubes, while only needing barcode reading stations in one or a few specific locations in the lab. Chain of custody sensors can be used to limit the number of reading stations or the number of times sample tube labels need to be read during the workflow. Chain of custody sensors allow trays to be only be placed at a reading station if a tube has been inserted or removed since the last reading. This can be further achieved by ensuring that manual insertion or removal is not part of the workflow once samples tube labels have been read by a reading station. In such a workflow, the only time that tubes are removed after barcode reading is via a robot arm process or other mechanically defined process. In some embodiments, the workflow can dictate that sample tubes are only removed by automation or by an operator while the tray is fixed at a barcode reading station.

In some embodiments, where the reading station cannot read all barcodes at the same time, the station can prioritize or limit the scan to the tube slots that have an unknown.

Separating the barcode reading optics from the tray can provide certain advantages. One advantage is that optics can read substantially perpendicularly. For example, the steep angles shown in FIG. 1c are not necessary because the rods with the optics can be raised along the height of each sample tube, allowing the optics to view each label head on/perpendicularly. Accordingly, the technical requirements for the optics can be much lower, which can improve reliability and improve cost significantly over embodiments where optics cannot be raised along the height of the sample tubes. Whereas the height of tubes could be a technical limit defined by the geometry of fixed optics, taller tubes can be accommodated with a flexible barcode reading station. For example, taller tubes can be accommodated by simply raising the optic rods higher above the surface of the tray being scanned. Any arbitrary reasonable length tube can now be scanned.

Different embodiments can have different numbers of rods. Some embodiments have a row of rods for every row of tubes—an array of rods—that allow the reading station to read the entire tray in one pass.

Another embodiment can have a single row of rods where the row of rods not only moves up and down, but also moves sideways. The system can move the row up and down in between the rows of the trays one after another in an action is like a flatbed scanner; the rods will rise relative to the tray every time it indexes a row. The advantage of that approach is its cost. So instead of needing to have a rod for every gap between tubes, you can just have one row of rods, no matter how many rows of tubes or trays that you have.

In some embodiments, the number of rods in a reading station is the same as the number of openings in tray, allowing a single motion to scan an entire tray. In other embodiments, the number of rods is substantially less than the number of openings. For example, in some embodiments, a single row of rods may be used, which requires a number of scans equal to the number of columns of openings (which may be one more than the number of columns of tube slots). In some embodiments, fewer rods than a single row may be used, requiring multiple scans per row, as well. In some embodiments, a single optical column can be used. Such an embodiment would result in substantially reduced cost, but substantially longer scan times than an embodiment having a large number of rods equal to the number of openings. Embodiments having fewer than the total rods needed can use a three-axis robot that moves along the rows, indexes between rows, and then moves up and down.

For example, a 10 by 10 tube tray (100 tube slots) could be used. The tubes are placed by an operator, resulting in random orientation of the barcodes, but once placed the tubes remain fixed in place relative to the tray. The operator takes the tray, places it in the barcode reading station, where the tray is indexed so that it is oriented to align itself with the rods. In one embodiment, the station has enough rods (e.g. 11×11–121 rods) to go into all the openings between each tube slot. These rods would rise up on the order of three to five seconds, scanning in a single motion. The rods can move at constant velocity and read as they rise past the barcodes. Each rod can read the barcodes substantially perpendicular to the barcodes rather than at a steep beam angle. Thus, on the order of three to five seconds, a reading station is able to read the barcode information for each of the 100 tubes with high reliability.

In another embodiment the barcode reading station include a single row (or multiple rows, but less than the number of columns of tubes) of optical reading rods. Every three to five seconds the rods advance to the next un-scanned row of openings, rise up, read the adjacent tubes, and then recede down below the tray. This can be accomplished by either moving the tray or by moving the row(s) of optical reading rods. Either the tray moves or the row of rods moves to the next holes in the tray. This embodiment takes multiple steps to read all of the tubes in the tray. However, if trays utilize presence sensors and have a half-full tray, for example, the barcode reading station might be able to complete the scan by rising to only the positions that are adjacent to tubes. This reduces the total amount of passes that are needed to read that half-empty tray.

Another embodiment that can be substantially cheaper uses a single rod that simply goes up through the openings between each set of tubes, making 121 different passes before scanning all sample tubes in a full tray.

Another advantage of separating the trays from the reading station is that the tray could be filled with tubes by the operator anywhere in the laboratory environment. An operator simply loads the tray and brings it back to a reading station where all the sensitive optics and the electronics are. A lab could have a whole lab full of low-cost plastic trays. If an operator spills something on them, the trays may be dishwasher safe or may be bleached. Trays may be impact resistant and dropped. Even trays utilizing presence switches may be relatively more robust and rugged than one having optics permanently affixed.

There are a few different ways the optical scanning rods can be used. One way is as part of a standalone station. The station reads all of the barcodes as described and then that identity information can be stored in one of many ways. In some embodiments, the station can transmit identity information to on-board memory of the tray. It could be uploaded to a database, such as an LIS (laboratory information system). Such an embodiment can be a standalone product. The station can be used for in-labbing, where a lab first knows what tubes have arrived inside the lab. The station can be used as part of a product database, where an individual analyzer uses it to log it into its database of on-board tubes. It can be part of any level of normal databases or information in a lab you could use it, or it can be part of the on-board storage of the rack itself.

FIG. 3 shows a top view of an exemplary barcode reading station suitable for a laboratory sample handler I/O. Station 48 is configured as a sample handler I/O station, where a plurality of trays 50-50c can be placed. An automation motion system can move the trays right or left, allowing trays to be input or output to the right. For example, an operator may load trays 50-50c from the right so that they can be automatically scanned and input into an analyzer, storage system, or other instrument. A single row of scanning rods 52 rises into opening in each tray as the tray incrementally passes by, allow each tray of fifty tubes to be scanned in six passes of rods 52, where each pass may take 3-5 seconds, allowing each tray to be fully scanned and moved into the instrument in approximately thirty seconds.

In some embodiments, the optical scanning rods can be integrated into other stations within the laboratory environment, including a pre-processing station. For example, an I/O configuration as shown in FIG. 3 can be placed wherever a station receives trays.

In some embodiments, a barcode reading station can be made more robust by utilizing multiple scan paths, taking advantage of the up and down/in and out motion that the rod use during a scan. If the vertical motion of the rods relative to the tray is defined as the z-axis, the rods an move up while aligned at one x-y location relative to the center of the openings in the tray and shift in the x-y plane before descending. This allows two slightly different scan paths to occur in a single scanning motion. FIG. 4 illustrates this concept. Scan path 110 represents the path taken during the ascending part of the scan. As shown in the upper right, the rods ascend at x-y position 112, which is approximately centered. This gives the first scan a predetermined perspective. Then, on the descending motion, rods can be shifted to follow scan path 120 (lower left). As seen, when observed more closely, path 120 scans tubes with a slight offset, at x-y offset 122 (lower right). Here, the dark lines represent the beam positions of path 120 at offset 122, while the dashed lines represent the beam paths of the beams at position 112, used on the upward motion. This allows a slightly different perspective that may allow for a more robust scan. For example, a barcode could have a defect when viewed along scan path 110 that does not exist along scan path 120, allowing the barcode to be successfully read, despite the defect. By moving the rod slightly off center of the openings in the x-y plan, the reading station can generate alternate scan paths.

Accordingly, the scan path can be adjusted for observed defects, found during an upward motion, on the down motion. Rods can be moved slightly in a lateral direction or transverse direction if the quality of the scan was insufficient on the rising scan path. Such adjustments could be made using linear motion systems to move the tray or the rods, such as linear actuators, motors, hydraulics, etc. Control for this adjusted path could be made by a processor that decodes the output of sensors in the rods. Furthermore, the controller could instruct the rod motion systems to perform multiple adjusted passes of rising up and down if the controller determines it needs to capture multiple scan paths if the first one or two paths fail to yield a satisfactory barcode reading. In some embodiments, the adjustment of the ascending and descending scan paths allows the reading station to capture substantially the entire surface of the tube if needed.

In some embodiments, the rods may adjust the scan path during the vertical motion or move in a non-linear path, such as forming a path that is more helical or elliptical. In some embodiments, the motion is a straight up and down motion.

A typical implementation might be for a customer to have an analyzer that has a couple of instrument stations, which would include at least one of the embodiments of barcode reading stations. The lab customer then may buy dozens or hundreds of trays for the sample tubes.

Figure 5:
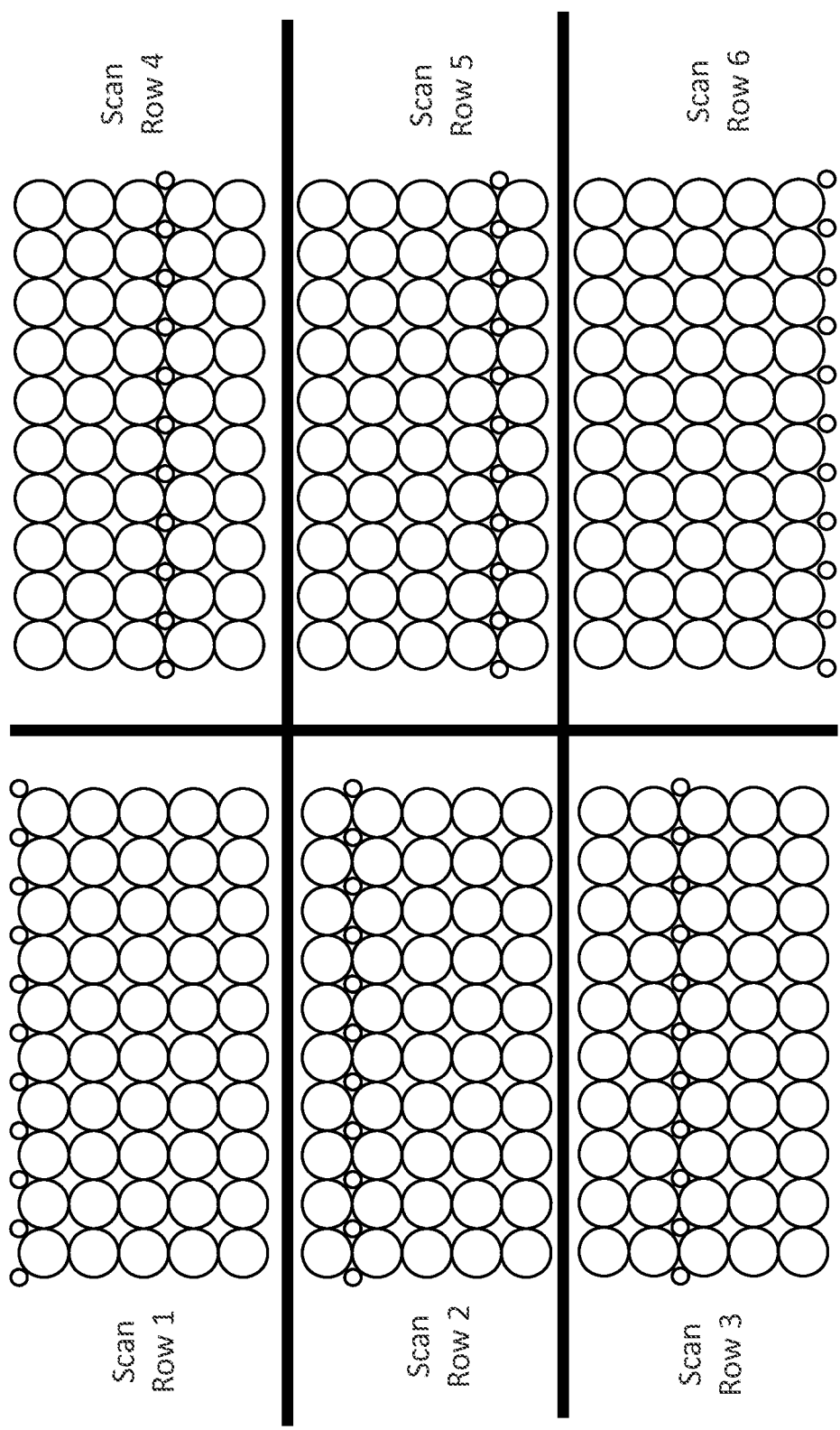
FIG. 5 is a diagrammatic top view of various scan passes for use with some embodiments.

FIG. 5 illustrates an example of how a row of rods may be used to sequentially scan a grid of tube holder slots in a tray. Six scans, one row at a time, are conducted to capture all perspectives of the tubes in the tray.

Figure 6:
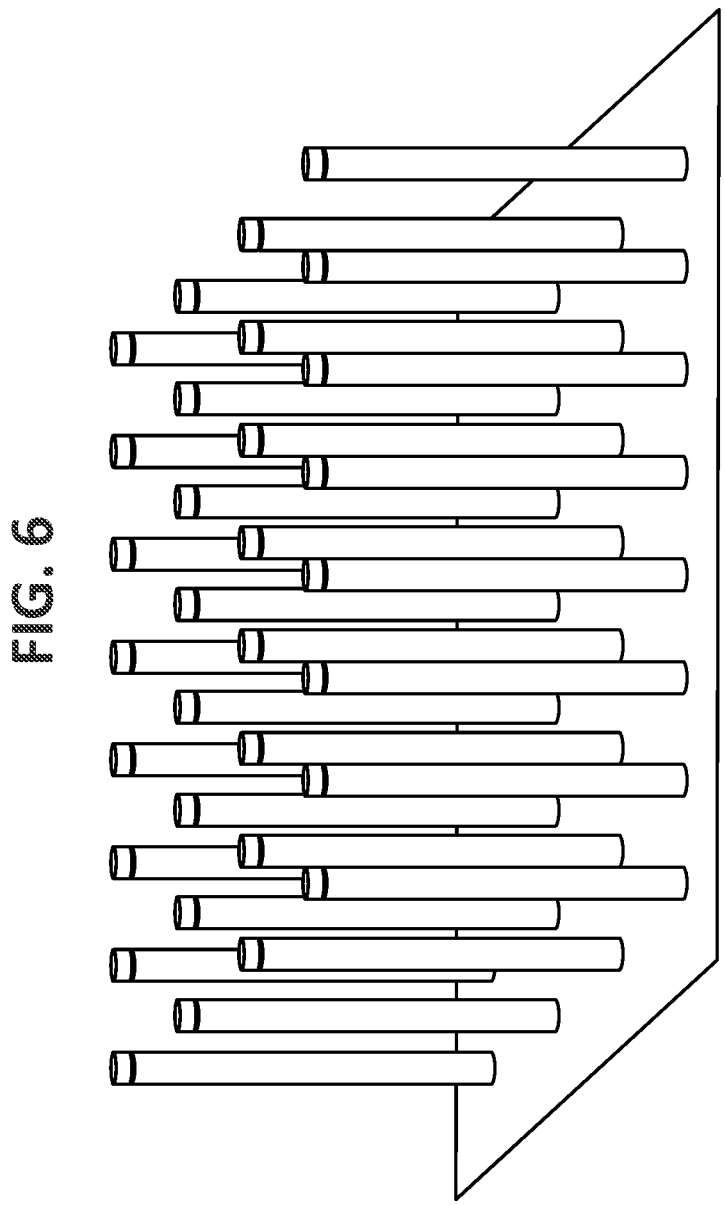
FIG. 6 is a perspective view of an exemplary barcode reading station for use with some embodiments.

FIG. 6 shows a perspective view of a multi-row embodiment of a barcode reading station, which allows all tubes to be simultaneously scanned.

Figure 7:
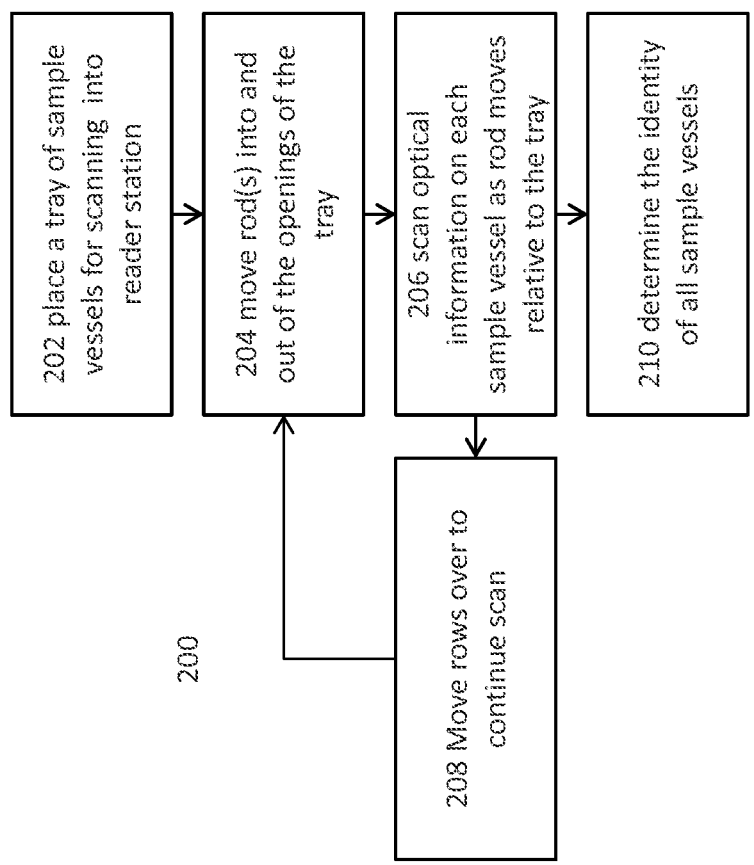
FIG. 7 is a flow chart illustrating use of a barcode reading station in accordance with some embodiments.

FIG. 7 shows an exemplary method 200 for using exemplary embodiments of a barcode reading station. After loading sample vessels into slots on a tray, at step 202, an automation system or operator places the tray of sample vessels (e.g., tubes) into the reader station for scanning. At step 204, the rods move relative to the tray, moving in and out of the openings of the tray. This can occur using any of the means discussed herein, including manually or mechanically lowering the tray or raising the rods. Preferably this occurs at substantially constant speed. At step 206, as the rods are moving, the optical elements of the rods scan any optical information of the tubes in the adjacent slots, scanning any barcodes. At step 208, if the number of rods is less than the total number of openings in the tray, the barcode reader station moves the rods horizontally relative to the tray to align the rods with the adjacent un-scanned openings or rows of openings and repeats the scanning action at step 204. At step 210, once all openings have been scanned, a processor interprets the barcode imaging data to determine the identity of each sample vessel in the tray.

In some embodiments, the rods comprise an array that allows scanning all of the plurality of openings in the tray substantially simultaneously. In some embodiments, a single row of rods is used to scan a single row simultaneously. In some embodiments, less than an entire row of rods is used, such as a single rod (or four adjacent rods in a square that allow a single tube to scanned in one motion), which allows scanning of all tubes sequentially. In some embodiments the rods are normally placed below the tray and rise up to scan the sample vessels. In some embodiments, the rods are placed overhead, allowing the rods to descend to scan the sample vessels. In some embodiments, the motion of step 204 includes moving along multiple scan paths, such as those disclosed with respect to FIG. 4.

What is claimed is:

1. A laboratory instrument comprising:
   one or more trays, each comprising a plurality of recesses, which are configured to hold a plurality of sample vessels, and a plurality of openings between the recesses; and
   one or more rods that are separate from the trays, each rod comprising optical elements configured to read barcode information on the sample vessels, wherein the rods are configured to move through the plurality of openings.

2. The laboratory instrument of claim 1, wherein the one or more rods are part of a station configured to identify the plurality of sample vessels as part of an in vitro diagnostics (IVD) workflow.

3. The laboratory instrument of claim 2, wherein the station is a standalone barcode reading station.

4. The laboratory instrument of claim 2, wherein the station is part of an analyzer and is accessible by an automation system that is configured to transport samples within the analyzer.

5. The laboratory instrument of claim 1, wherein the optical elements are configured to read the barcode information substantially perpendicularly.

6. The laboratory instrument of claim 1, wherein the optical elements are configured to read the barcode information while the rods move relative to the tray.

7. The laboratory instrument of claim 1, wherein the one or more rods are configured to automatically rise from below the one or more trays after each tray is placed above the rods.

8. The laboratory instrument of claim 1, wherein the one or more rods are configured to enter the plurality of openings from above the one or more trays.

9. The laboratory instrument of claim 1, wherein the one or more rods are fixed and configured to read barcode information while the one or more trays are lowered onto the rods.

10. The laboratory instrument of claim 1, wherein the one or more rods are configured to enter the plurality of openings from above the one or more trays while the trays are raised to the rods.

11. The laboratory instrument of claim 1, wherein the one or more rods comprise an array of rods configured to allow all the sample vessels to be scanned substantially simultaneously.

12. The laboratory instrument of claim 1, wherein the one or more rods comprise at least one row of rods configured to allow all the rows of sample vessels to be scanned sequentially.

13. A method for scanning optical information on a plurality of sample vessels comprising steps of:
   placing a tray of sample vessels for scanning, wherein the tray comprises a plurality of openings, each opening configured to receive a rod that contains a plurality of optical elements;
   moving at least one rod into and out of the openings of the tray; and
   scanning optical information on each sample vessel as the at least one rod moves relative to the tray.

14. The method of claim 13, wherein the step of moving comprises moving an array of rods into all of the plurality of openings substantially simultaneously.

15. The method of claim 13, wherein the step of scanning comprises scanning optical information of all of the plurality of the sample vessels substantially simultaneously.

16. The method of claim 13, wherein the optical information is barcode information.

17. The method of claim 13, wherein the step of moving comprises moving at least one row of rods into at least one row of the plurality of openings substantially simultaneously.

18. The method of claim 13, wherein the step of moving comprises moving a single rod into at least one row of the plurality of openings sequentially.

19. The method of claim 13, wherein the step of scanning comprises scanning optical information of at least one row of the plurality of the sample vessels substantially simultaneously.

20. The method of claim 13, wherein the step of moving comprises moving the at least one rod from below the tray.

21. The method of claim 13, wherein the step of moving comprises moving the at least one rod from above the tray.

22. The method of claim 13, wherein the step of moving comprises lowering the tray onto the rods.

23. The method of claim 13, wherein the step of moving comprises adjusting the motion of the at least one rod to allow the rod to travel in multiple available scan paths with at least one of the plurality of openings.

* * * * *